United States Patent [19]

Yu

[11] 4,205,003
[45] May 27, 1980

[54] 2-[5-(4-CHLOROPHENYL)FURFURYL]-1,3,-PROPANEDIOL

[75] Inventor: Chia-Nien Yu, Norwich, N.Y.
[73] Assignee: Morton-Norwich Products, Inc., Norwich, N.Y.
[21] Appl. No.: 21,472
[22] Filed: Mar. 19, 1979
[51] Int. Cl.² .................................................. C07D 307/46
[52] U.S. Cl. .................................... 260/347.8; 424/285
[58] Field of Search ........................................ 260/347.8

[56] References Cited

U.S. PATENT DOCUMENTS 3,931,247  1/1976  Pelosi ........................... 260/347.8 X Primary Examiner—Richard Raymond
Attorney, Agent, or Firm—Anthony J. Franze

[57] ABSTRACT

2-[5-(4-Chlorophenyl)furfuryl]-1,3,-propanediol is useful as an anti-inflammatory and antifungal agent.

1 Claim, No Drawings

2-[5-(4-CHLOROPHENYL)FURFURYL]-1,3,-PROPANEDIOL

This invention is concerned with the compound 2-[5-(4-chlorophenyl)furfuryl]-1,3,-propanediol. It possesses pharmacological properties. In particular, it displays anti-inflammatory activity when administered per os at a dose of about 300 mg/kg suspended in a vehicle such as aqueous methyl cellulose to rats concomitantly receiving the edema producing agent carrageenin. Edema normally elicited by carrageenin is markedly reduced.

This compound also exhibits antifungal activity. At a concentration of about 100 mcg/ml it inhibits the growth of *Microsporum canis* in the commonly employed in vitro agar dilution method for detecting antifungal properties.

This compound can be combined in known fashion with various compatible excipients and adjuvants to provide pharmaceutical compositions.

The method currently preferred for the preparation of the compound of this invention is described as follows:

A. Diethyl [5-(4-Chlorophenyl)furfurylidene]malonate

Diethyl malonate (88 g, 0.55 mole) and 5-(p-chlorophenyl)-2-furaldehyde (104 g, 0.50 mole) were placed in 1.0 liter of benzene containing benzoic acid (10 g) and piperidine (18 ml). The 2.0 liter flask was equipped with a Dean-Stark trap for water removal, and the mixture was refluxed for 4 hours on a steam bath. The mixture was concentrated to an oil under reduced pressure. Washing the residue with benzene (500 ml) yielded a dark solid which was recrystallized from cyclohexane yielding yellow product (111 g, 64% yeild), m.p. 78°–80°.

A sample was recrystallized from alcohol to yield yellow crystals of m.p. 78°–80°.

Anal. Calc'd. for $C_{18}H_7ClO_5$: C, 61.98; H, 4.91. Found: C, 62.04; H, 4,87.

B. 2-(5-4-Chlorophenylfurfuryl)-1,3-propanediol

A mixture of 42.7 g (0.12 m) of A. in 220 ml of alcohol and 1 g. of 5% palladium on carbon (50% water) was subjected to reduction. After theoretical hydrogen uptake, the mixture was filtered and the filtrate was concentrated to a liquid residue.

Lithium aluminum hydride (LAH) (50 g, 0.14 m) was added gradually in about 15 min. to 2.5 l. of anhydrous ether with stirring. After slight cooling, the above liquid residue in 450 ml of anhydrous ether was added dropwise (~45 min) such that a gentle reflux of ether was maintained. The mixture was further heated at reflux in a water bath for 1½ hr. After cooling, 350 ml of water was added cautiously (1½ hr) to decompose the excess LAH.

After standing overnight, the top ether layer was separated, dried over $MgSO_4$ and concentrated to give 25 g of somewhat gummy white solid. Repeated recrystallizations from methylcyclohexane gave 6.5 g (20% yield). m.p. 99°–102°.

Anal. Calc'd. for $C_{14}H_{15}ClO_3$: C, 63.04; H, 5.67. Found: C, 63.43; H, 5.82.

What is claimed is:

1. The compound 2-[5-(4-chlorophenyl)furfuryl]-1,3,-propanediol.

* * * * *